US012655096B2

(12) United States Patent
Kolesa et al.

(10) Patent No.: US 12,655,096 B2
(45) Date of Patent: Jun. 16, 2026

(54) CRYSTALLINE POLYMORPHS OF RIGOSERTIB SODIUM

(71) Applicant: ASSIA CHEMICAL INDUSTRIES LTD., Tel Aviv (IL)

(72) Inventors: Pavel Kolesa, Hlubocec (CZ); Roman Gabriel, Olomouc (CZ); Alexandr Jegorov, Dobra Voda U Ceských Budiljovic (CZ)

(73) Assignee: ASSIA CHEMICAL INDUSTRIES LTD., Tel Aviv (IL)

( * ) Notice: Subject to any disclaimer, the term of this patent is extended or adjusted under 35 U.S.C. 154(b) by 17 days.

(21) Appl. No.: 18/635,160

(22) Filed: Apr. 15, 2024

(65) Prior Publication Data

US 2024/0279167 A1 Aug. 22, 2024

Related U.S. Application Data

(62) Division of application No. 17/288,590, filed as application No. PCT/US2019/057763 on Oct. 24, 2019, now Pat. No. 11,981,624.

(60) Provisional application No. 62/750,880, filed on Oct. 26, 2018.

(51) Int. Cl.
*C07C 317/28* (2006.01)

(52) U.S. Cl.
CPC ........ *C07C 317/28* (2013.01); *C07B 2200/13* (2013.01); *C07C 2601/14* (2017.05)

(58) Field of Classification Search
CPC . A61P 35/00; C07B 2200/13; C07C 2601/14; C07C 317/28
See application file for complete search history.

(56) References Cited

U.S. PATENT DOCUMENTS 8,476,320 B2 * 7/2013 Bell ..................... A61K 31/496
514/710
2009/0036462 A1 * 2/2009 Bell ..................... A61K 47/10
514/357

FOREIGN PATENT DOCUMENTS

CN 109867670 A 6/2019
CN 110981770 A 4/2020
WO 2015074281 A1 5/2015

OTHER PUBLICATIONS

Mino R. Caira "Crystalline Polymorphism of Organic Compounds," Topics in Current Chemistry, vol. 8, pp. 163-208 (1998).
International Search Report and Written Opinion of the International Searching Authority issued in corresponding application PCT/US2019/057763 mailed Dec. 18, 2019 (15 pages).
M.V. Ramana Reddy, et al., "Discovery of a Clinical Stage Multi-Kinase Inhibitor Sodium (E)-2-{2-Methoxy-5-[(2',4',6'-trimethoxystyrylsulfonyl)methyl]phenylamino}-acetate (ON 01910. Na): Synthesis, Structure-Activity Relationship, and Biological Activity", Journal of Medicine Chemistry, 2011, vol. 54, 6254-6276.
Venkat R. Pallela, et al., "Hydrothiolation of benzyl mercaptan to arylacetylene: application to the synthesis of (E) and (Z)-isomers of ON 01910-Na (Rigosertib®), a phase III clinical stage anti-cancer agent†", Org. Biomol. Chem., 2013, 11, 1964-1977.
Hardikkumar H. Patel, et al., "Determination of Degradation Kinetics and Effect of Anion Exchange Resin on Dissolution of Novel Anticancer Drug Rigosertib in Acidic Conditions", AAPS PharmSciTech, vol. 19, No. 1, Jan. 2018, pp. 93-100.
Healy et al., "Pharmeceutical solvates, hydrates and amorphous forms: A special emphasis of cocrystals," Advanced Drug Delivery Reviews, 117, pp. 25-46 (2017).
Hardikkumar H. Patel, et al., "Effect of β-cyclodextrin and Hydroxypropyl β-cyclodextrin on Aqueous Stability, Solubility and Dissolution of Novel Anti-cancer Drug Rigosertib", Journal of Pharmaceutical Research International, vol. 21, No. 3, pp. 1-20 (2018).

* cited by examiner

*Primary Examiner* — Andrew D Kosar
*Assistant Examiner* — Blaine G Doletski
(74) *Attorney, Agent, or Firm* — Carter, DeLuca & Farrell, LLP

(57) ABSTRACT

The present disclosure encompasses crystalline polymorphs of Rigosertib Sodium, processes for preparation thereof, and pharmaceutical compositions thereof.

15 Claims, 12 Drawing Sheets

Figure 1. X-Ray Powder Diffraction Pattern of Rigosertib Sodium Form A, obtained according to example 1.
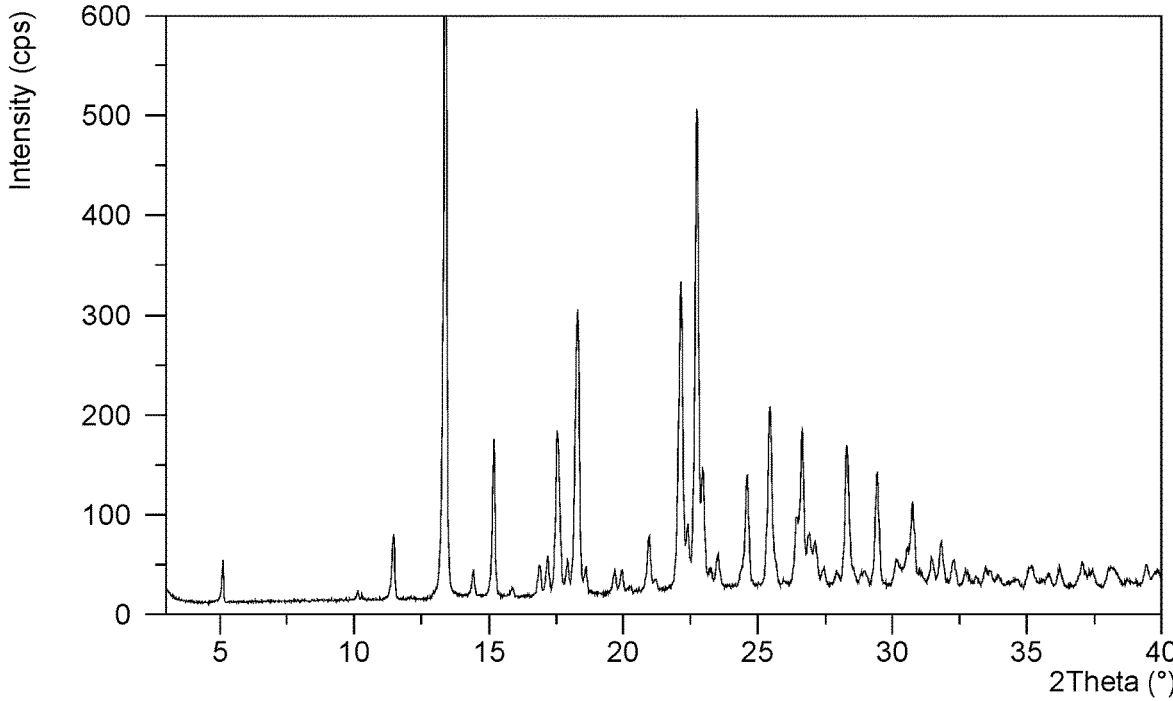

Figure 2. X-Ray Powder Diffraction Pattern of Rigosertib Sodium Form B, obtained according to example 4.
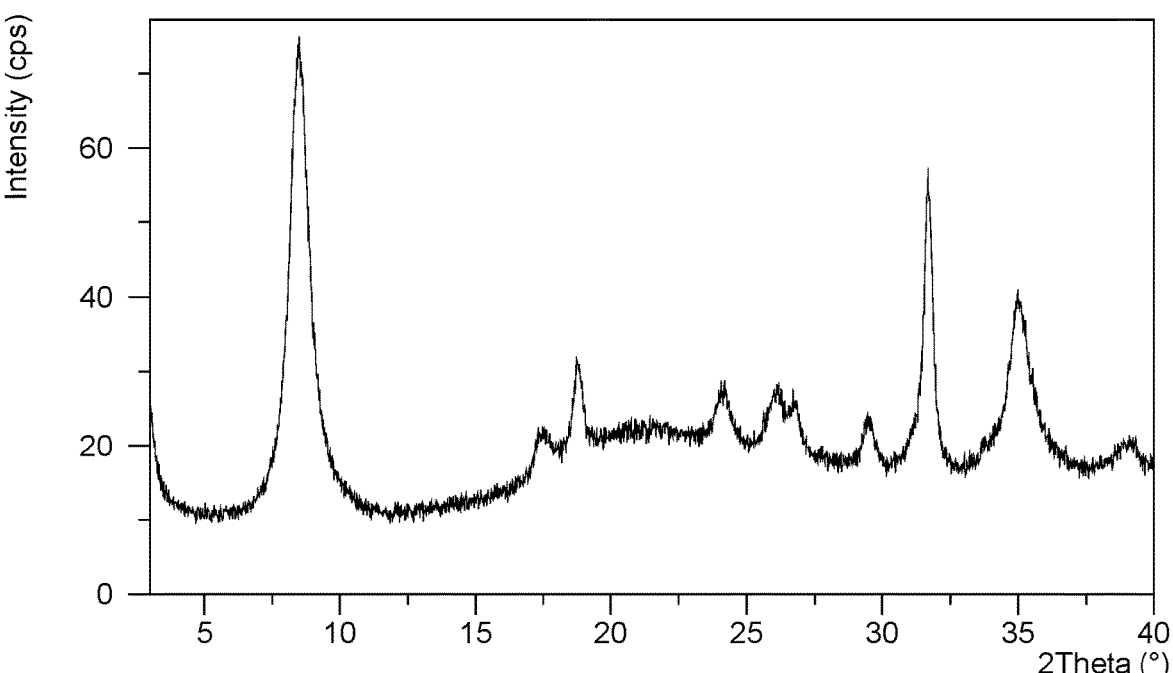

Figure 3. X-Ray Powder Diffraction Pattern of Rigosertib Sodium Form C, obtained according to example 5.
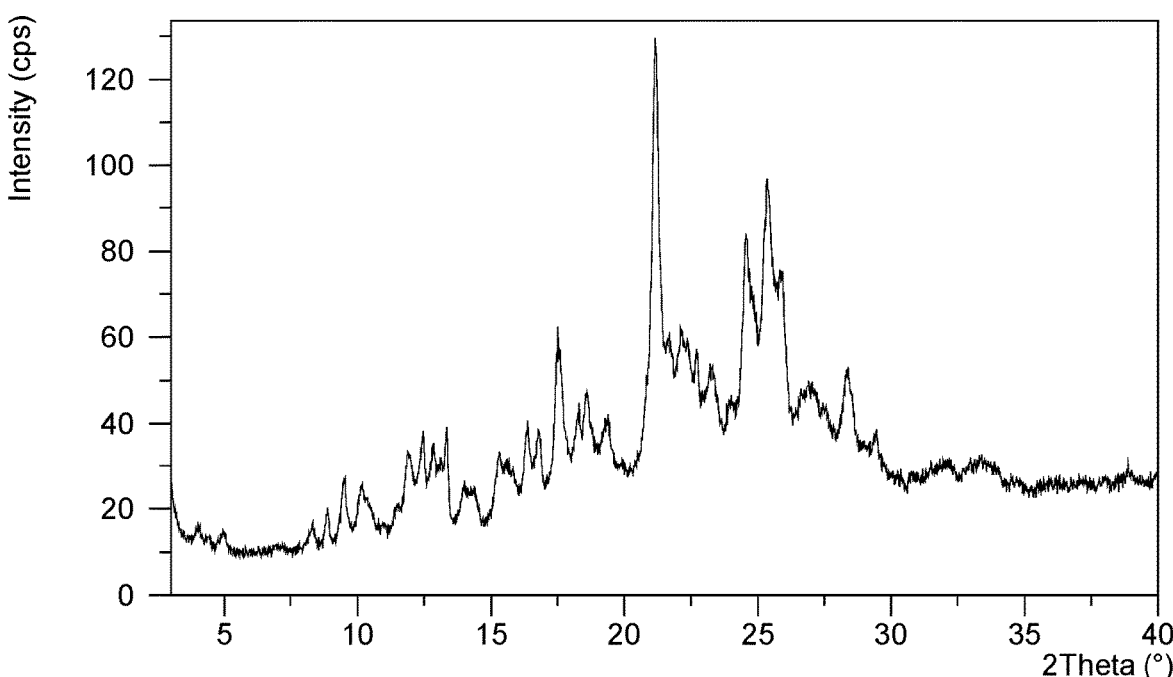

Figure 4. X-Ray Powder Diffraction Pattern of Rigosertib Sodium Form D obtained in example 6.
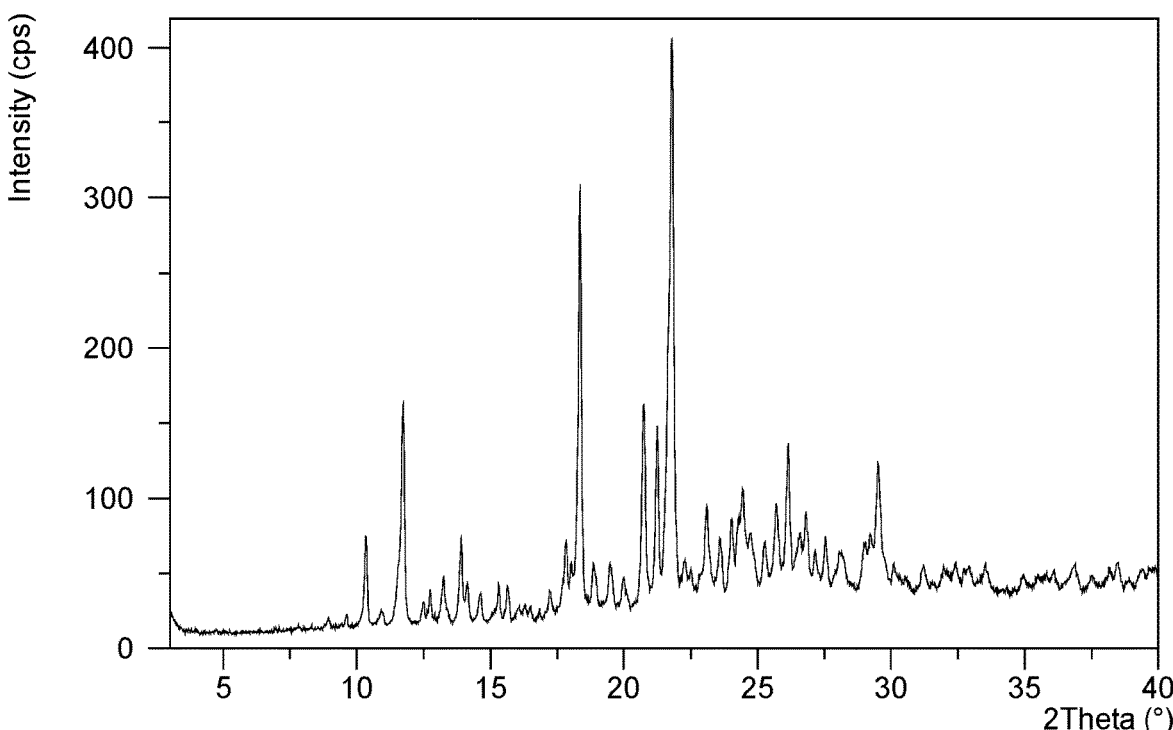

Figure 5. X-Ray Powder Diffraction Pattern of Rigosertib Sodium Form E obtained in example 7.
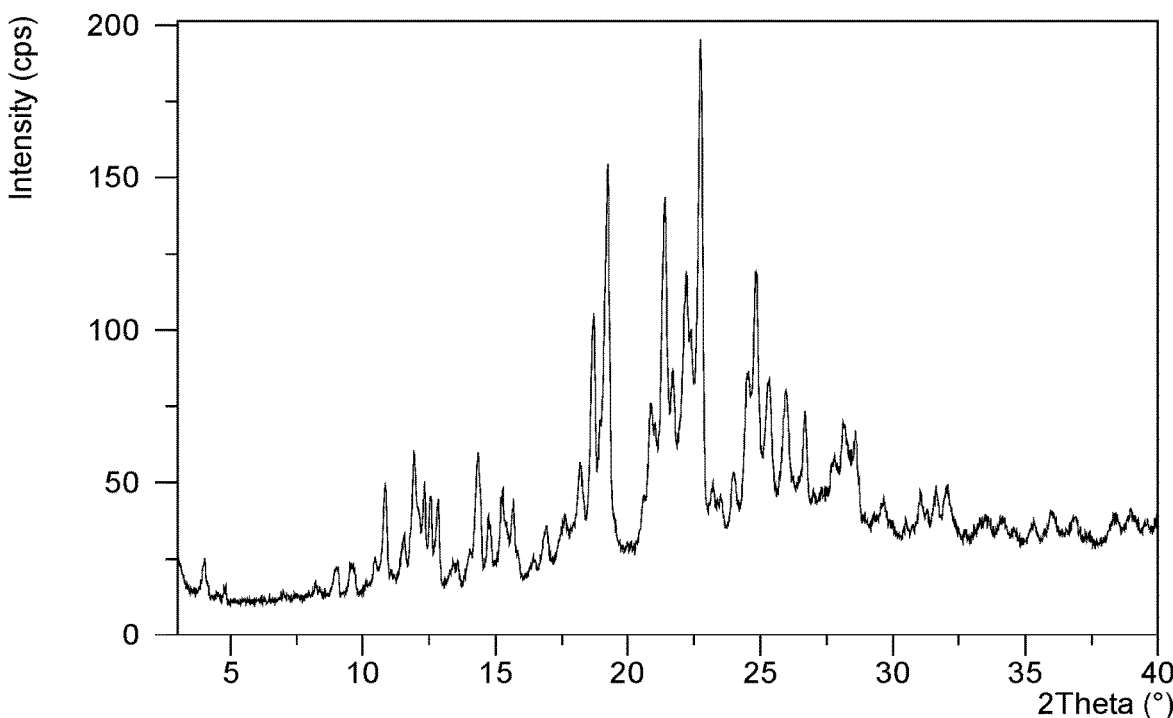

Figure 6. X-Ray Powder Diffraction Pattern of Rigosertib Sodium substantially amorphous which was used as the starting material for examples 4-6.
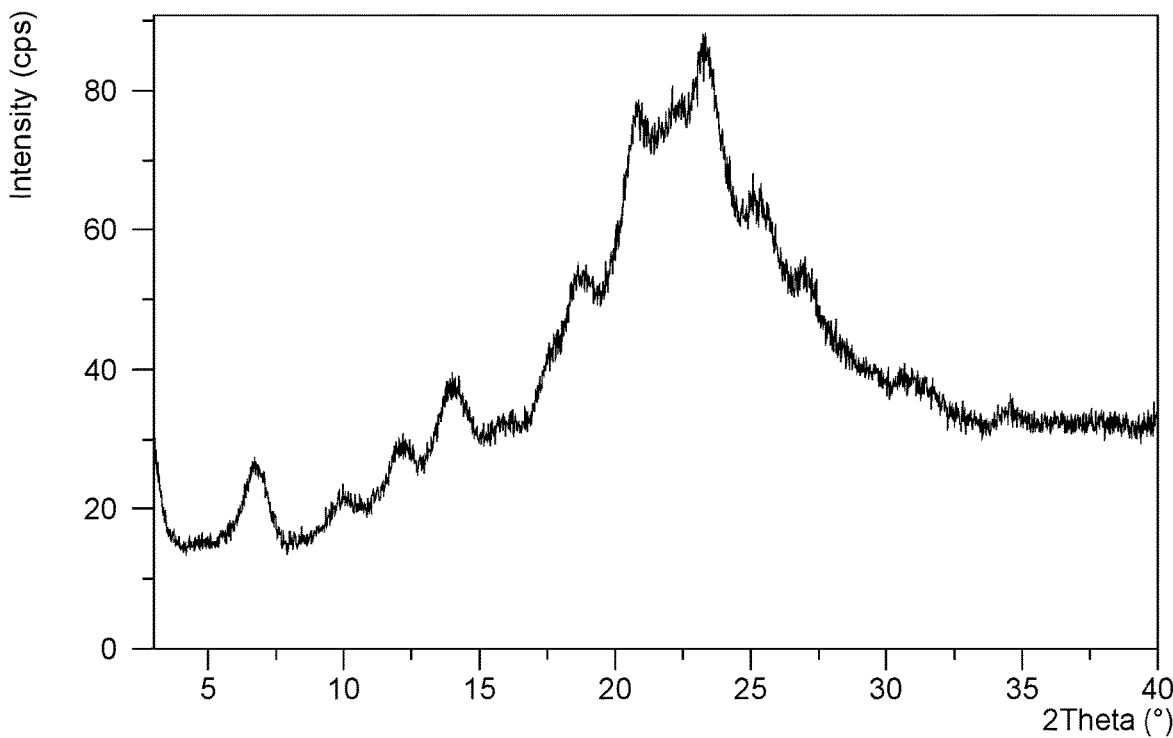

Figure 7. Solid state 13C NMR spectrum of Form A of Rigosertib Sodium (full range 0-200ppm).
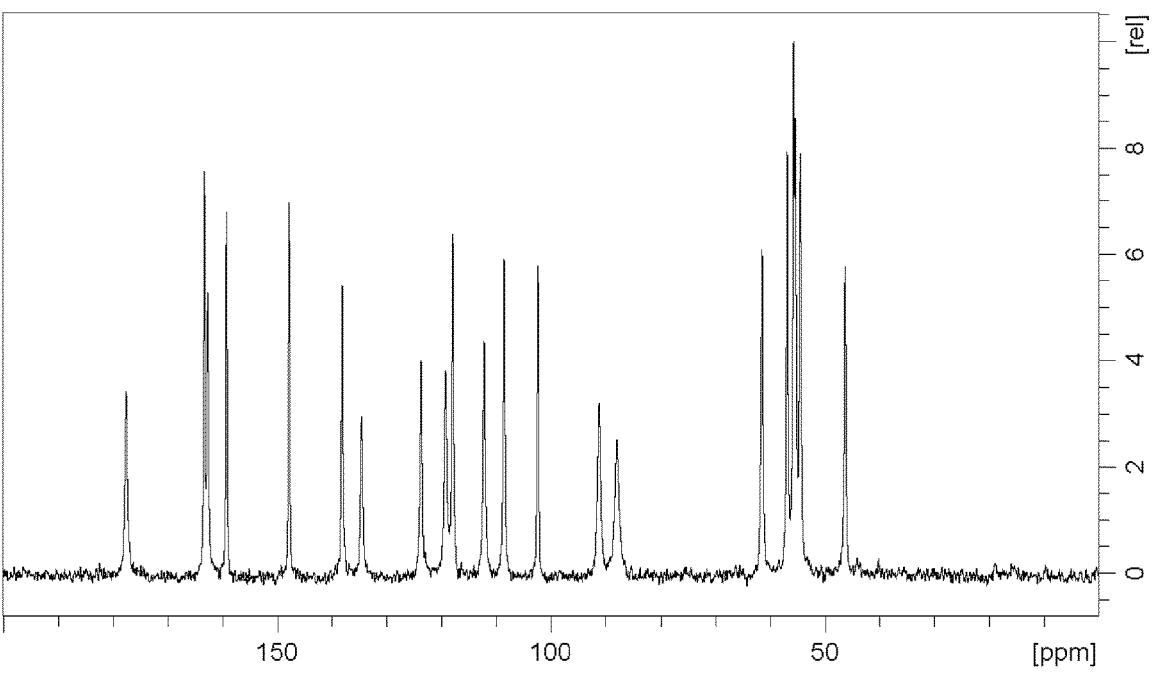

Figure 8. Solid state 13C NMR spectrum of Form A of Rigosertib Sodium (range 0-100ppm).
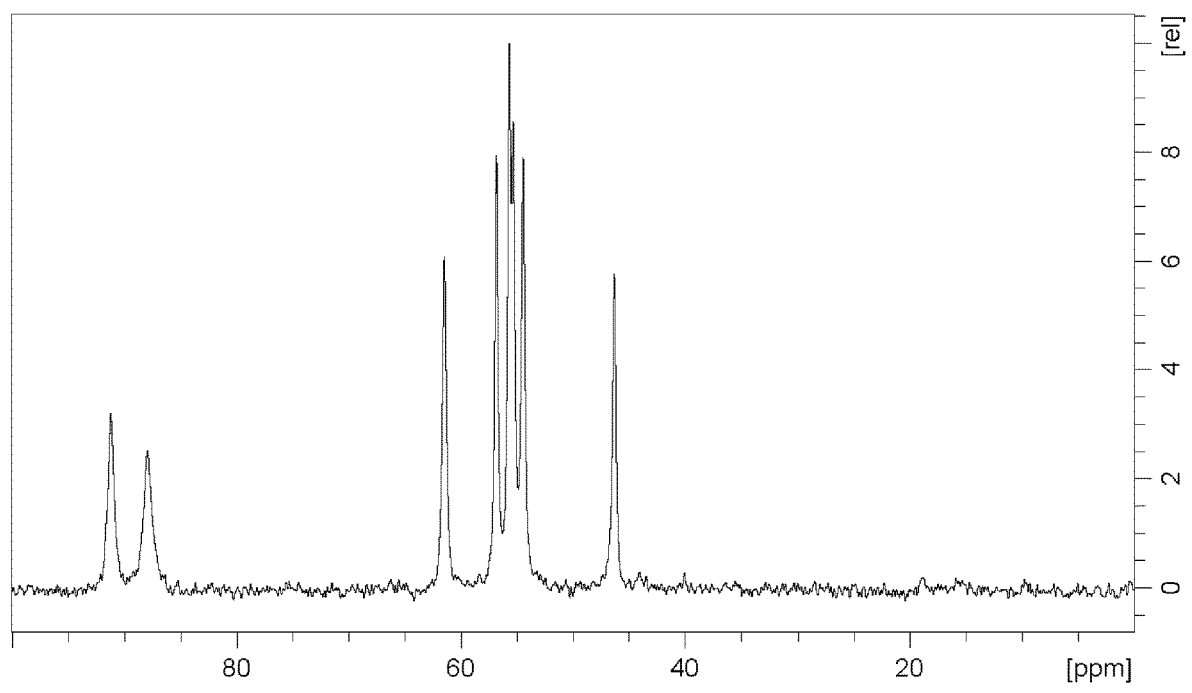

Figure 9. Solid state 13C NMR spectrum of Form A of Rigosertib Sodium (range 100-200ppm).
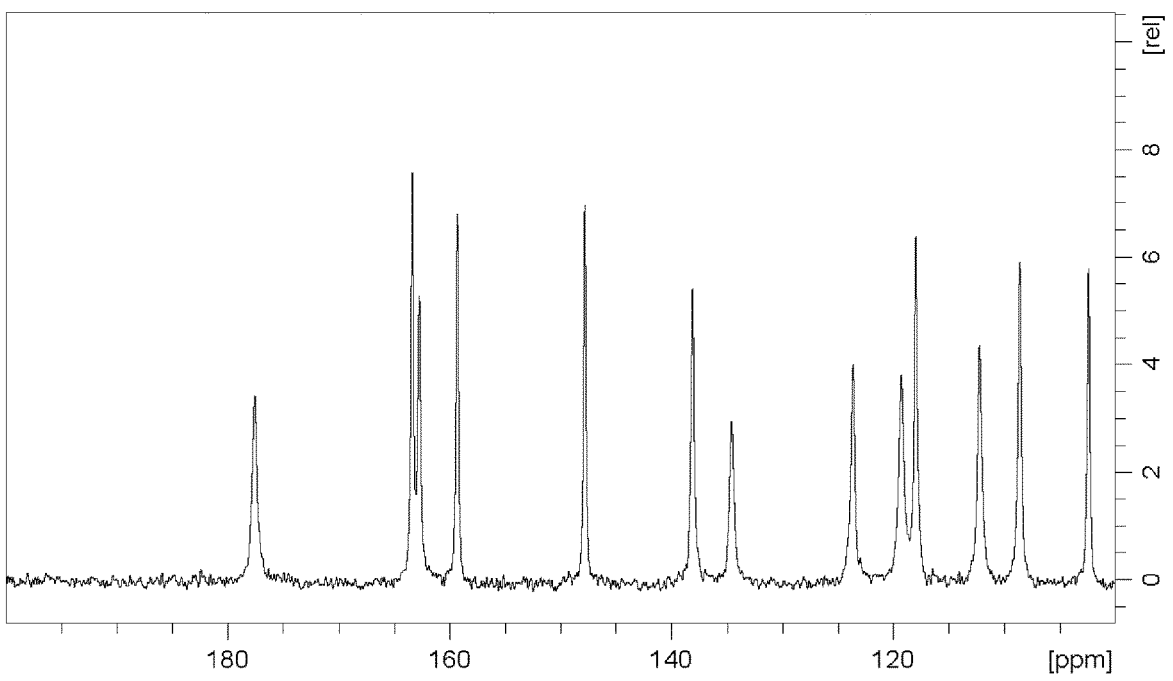

Figure 10. Solid state 13C NMR spectrum of Form E of Rigosertib Sodium (full range 0-200ppm).
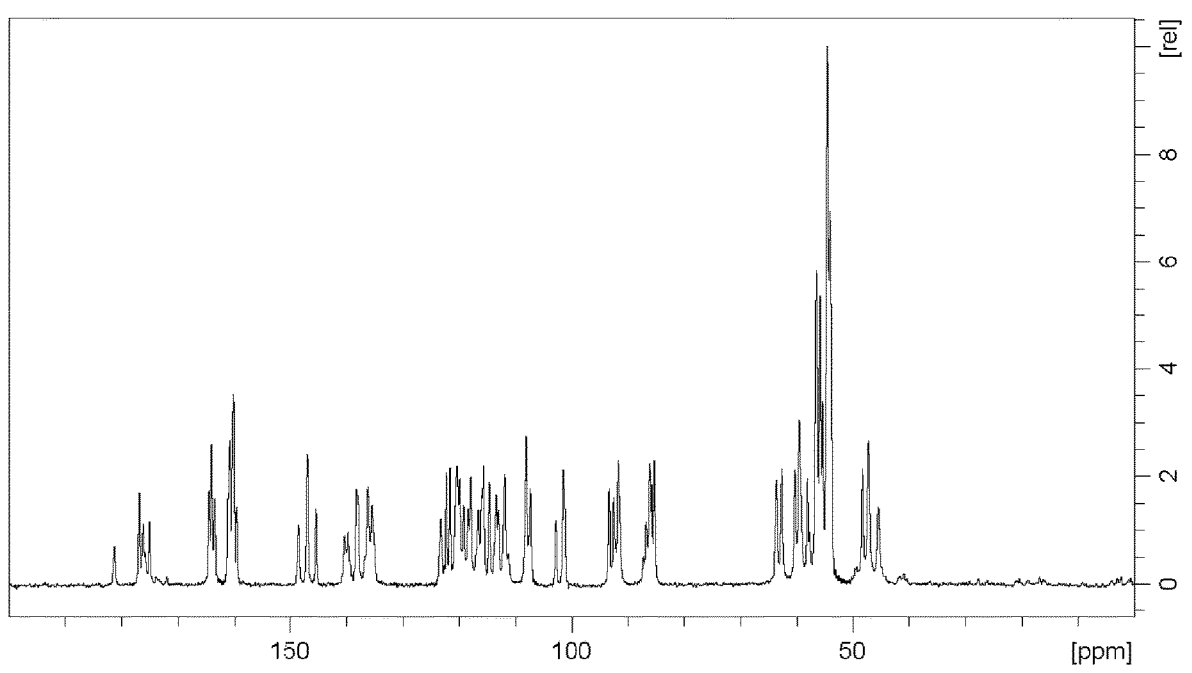

Figure 11. Solid state 13C NMR spectrum of Form E of Rigosertib Sodium (range 0-100ppm).
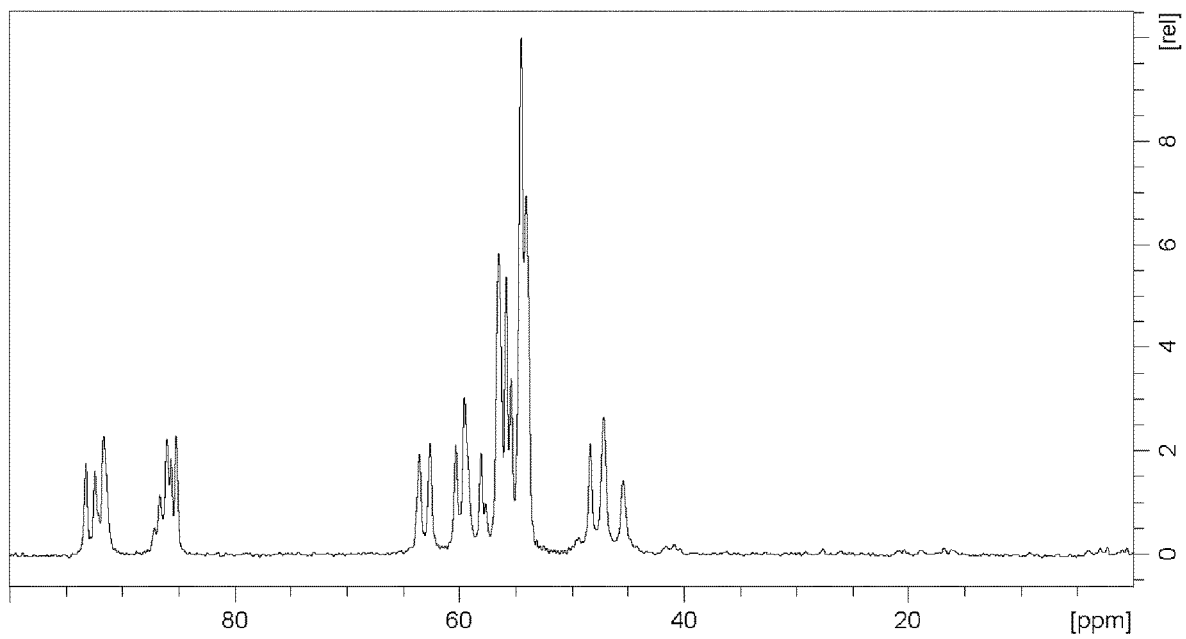

Figure 12. Solid state 13C NMR spectrum of Form E of Rigosertib Sodium (range 100-200ppm).
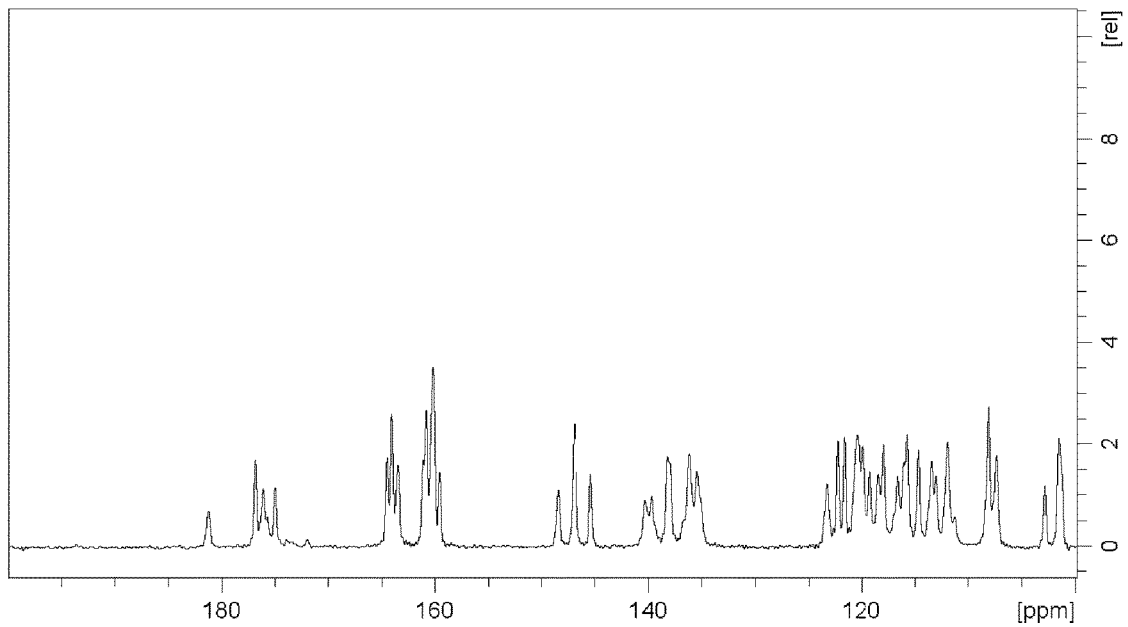

CRYSTALLINE POLYMORPHS OF RIGOSERTIB SODIUM

CROSS REFERENCE TO RELATED APPLICATIONS

This application is a Divisional application of U.S. patent application Ser. No. 17/288,590, filed on Apr. 26, 2021, which is a National Stage of, and claims priority to and the benefit of, International Patent Application No. PCT/US2019/057763 filed Oct. 24, 2019, which, in turn, claims the benefit of and priority to, U.S. Provisional Patent Application No. 62/750,880, filed Oct. 26, 2018, the entire disclosures of each of which are incorporated by reference herein.

TECHNICAL FIELD

The present disclosure encompasses crystalline polymorphs of Rigosertib Sodium, processes for preparation thereof, and pharmaceutical compositions thereof.

BACKGROUND

Rigosertib has the chemical name 2-[(2-Methoxy-5-{[(E)-2-(2,4,6-trimethoxyphenyl)ethenesulfonyl] methyl}phenyl)amino]acetic acid. Rigosertib has the following chemical structure:

Rigosertib sodium is a novel and targeted anti-cancer compound currently in a Phase 3 study for the treatment of MDS, a group of rare hematologic malignancies. Specifically, Rigosertib sodium is under development for the treatment of Chronic Myelomonocytic leukemia and for Myelodysplastic syndromes.

Rigosertib is described in U.S. Pat. No. 7,598,232 (compound 4). Some procedures for the preparation of Rigosertib Sodium are described in some articles without all details. Amorphous Rigosertib Sodium is described in U.S. Pat. No. 8,476,320 as "off-white to yellow amorphous solid that readily absorbs water after complete drying". Different salts of Rigosertib, other than sodium salt, are described in PCT application WO 2015/074281.

Polymorphism, the occurrence of different crystalline forms, is a property of some molecules and molecular complexes. A single molecule, like Rigosertib Sodium, may give rise to a variety of polymorphs having distinct crystal structures and physical properties like melting point, thermal behaviors (e.g., measured by thermogravimetric analysis— "TGA", or differential scanning calorimetry—"DSC"), X-ray powder diffraction (XRPD) pattern, infrared absorption fingerprint, and solid state ($^{13}$C) NMR spectrum. One or more of these techniques may be used to distinguish different polymorphic forms of a compound.

Different salts and solid state forms (including solvated forms) of an active pharmaceutical ingredient may possess different properties. Such variations in the properties of different salts and solid state forms and solvates may provide a basis for improving formulation, for example, by facilitating better processing or handling characteristics, improving the dissolution profile, or improving stability (polymorph as well as chemical stability) and shelf-life. These variations in the properties of different salts and solid state forms and solvates may also offer improvements to the final dosage form, for instance, if they serve to improve bioavailability. Different salts and solid state forms and solvates of an active pharmaceutical ingredient may also give rise to a variety of polymorphs or crystalline forms, which may in turn provide additional opportunities to use variations in the properties and characteristics of a solid active pharmaceutical ingredient.

Discovering new solid state forms and solvates of a pharmaceutical product may yield materials having desirable processing properties, such as ease of handling, ease of processing, storage stability, and ease of purification or as desirable intermediate crystal forms that facilitate conversion to other polymorphic forms. New solid state forms of a pharmaceutically useful compound can also provide an opportunity to improve the performance characteristics of a pharmaceutical product. It enlarges the repertoire of materials that a formulation scientist has available for formulation optimization, for example by providing a product with different properties, e.g., a different crystal habit, higher crystallinity, or polymorphic stability, which may offer better processing or handling characteristics, improved dissolution profile, or improved shelf-life (chemical/physical stability). For at least these reasons, there is a need for additional solid state forms (including solvated forms) of Rigosertib Sodium.

SUMMARY OF THE DISCLOSURE

The present disclosure provides crystalline polymorphs of Rigosertib Sodium, processes for preparation thereof, and pharmaceutical compositions thereof. These crystalline polymorphs can be used to prepare other forms of Rigosertib Sodium, Rigosertib and solid state forms thereof, or other salts of Rigosertib and solid state forms thereof.

In particular, the present disclosure relates to solid state forms of Rigosertib Sodium designated as Forms A-E (defined herein). The present disclosure also provides the uses of any one or combination of the above described solid state forms of Rigosertib Sodium for preparing other solid state forms of Rigosertib Sodium. The present disclosure further provides the use of any one or combination of the above described solid state forms of Rigosertib Sodium for preparing Rigosertib and solid state forms thereof, other salts of Rigosertib and solid state forms thereof.

The present disclosure further provides processes for preparing Rigosertib Sodium solid state forms thereof.

In another embodiment, the present disclosure provides crystalline polymorphs of Rigosertib Sodium for use in medicine, in embodiments for the treatment of Chronic myelomonocytic leukemia and Myelodysplastic syndromes.

The present disclosure also encompasses the uses of any one of the above described crystalline polymorphs of Rigosertib Sodium of the present disclosure for the preparation of pharmaceutical compositions and/or formulations.

In another aspect, the present disclosure provides pharmaceutical compositions including crystalline polymorphs of Rigosertib Sodium according to the present disclosure.

In yet another embodiment, the present disclosure encompasses pharmaceutical formulations including any one of the above described crystalline polymorphs of Rigosertib Sodium and/or combinations thereof, and at least one pharmaceutically acceptable excipient.

The present disclosure comprises processes for preparing the above mentioned pharmaceutical formulations of Rigosertib Sodium including any one of the above described crystalline polymorphs and at least one pharmaceutically acceptable excipient.

The crystalline polymorphs defined herein and/or combinations thereof as well as the pharmaceutical compositions or formulations of the crystalline polymorphs of Rigosertib Sodium may be used as medicaments, particularly for the treatment of Chronic myelomonocytic leukemia and Myelodysplastic syndromes.

The present disclosure also provides methods of treating Chronic myelomonocytic leukemia and Myelodysplastic syndromes, which include administering a therapeutically effective amount of any one of the crystalline polymorphs of Rigosertib Sodium of the present disclosure, or at least one of the above pharmaceutical compositions or formulations, to a subject suffering from Chronic myelomonocytic leukemia and Myelodysplastic syndromes, or otherwise in need of the treatment.

The present disclosure also provides the uses of any one of the solid state forms of Rigosertib Sodium of the present disclosure, or at least one of the above pharmaceutical compositions or formulations, for the manufacture of medicaments for treating Chronic myelomonocytic leukemia and Myelodysplastic syndromes.

BRIEF DESCRIPTION OF THE DRAWINGS

FIG. 1 shows a characteristic X-ray powder diffraction pattern (XRPD) of Rigosertib Sodium Form A.

FIG. 2 shows a characteristic X-ray powder diffraction pattern (XRPD) of Rigosertib Sodium Form B.

FIG. 3 shows a characteristic X-ray powder diffraction pattern (XRPD) of Rigosertib Sodium Form C.

FIG. 4 shows a characteristic X-ray powder diffraction pattern (XRPD) of Rigosertib Sodium Form D.

FIG. 5 shows a characteristic X-ray powder diffraction pattern (XRPD) of Rigosertib Sodium Form E.

FIG. 6 shows a characteristic X-ray powder diffraction pattern (XRPD) of substantially amorphous Rigosertib Sodium.

FIG. 7 shows a solid state 13C NMR spectrum of Form A of Rigosertib Sodium (full range 0-200 ppm).

FIG. 8 shows a solid state 13C NMR spectrum of Form A of Rigosertib Sodium (range 0-100 ppm).

FIG. 9 shows a solid state 13C NMR spectrum of Form A of Rigosertib Sodium (range 100-200 ppm).

FIG. 10 shows a solid state 13C NMR spectrum of Form E of Rigosertib Sodium (full range 0-200 ppm).

FIG. 11 shows a solid state 13C NMR spectrum of Form E of Rigosertib Sodium (range 0-100 ppm).

FIG. 12 shows a solid state 13C NMR spectrum of Form E of Rigosertib Sodium (range 100-200 ppm).

DETAILED DESCRIPTION OF THE DISCLOSURE

The present disclosure encompasses crystalline polymorphs of Rigosertib Sodium, processes for preparation thereof, and pharmaceutical compositions comprising at least one of, or a combination of, these solid state forms. The disclosure also relates to the conversion of Rigosertib Sodium and its solid state forms to other solid state forms of Rigosertib Sodium.

The Rigosertib Sodium and solid state forms thereof according to the present disclosure may have advantageous properties selected from at least one of the following: chemical or polymorphic purity, flowability, solubility, dissolution rate, bioavailability, morphology or crystal habit, stability—such as chemical stability as well as thermal and mechanical stability with respect to polymorphic conversion, stability towards dehydration and/or storage stability, low content of residual solvent, a lower degree of hygroscopicity, flowability, and advantageous processing and handling characteristics such as compressibility, and bulk density.

A solid state form, such as a crystal form or an amorphous form, may be referred to herein as being characterized by graphical data "as depicted in" or "as substantially depicted in" a Figure. Such data include, for example, powder X-ray diffractograms and solid state NMR spectra. As is well-known in the art, the graphical data potentially provides additional technical information to further define the respective solid state form (a so-called "fingerprint") which cannot necessarily be described by reference to numerical values or peak positions alone. In any event, the skilled person will understand that such graphical representations of data may be subject to small variations, e.g., in peak relative intensities and peak positions due to certain factors such as, but not limited to, variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystal form of Rigosertib Sodium referred to herein as being characterized by graphical data "as depicted in" or "as substantially depicted in" a Figure will thus be understood to include any crystal forms of Rigosertib Sodium characterized with the graphical data having such small variations, as are well known to the skilled person, in comparison with the Figure.

A solid state form (or polymorph) may be referred to herein as polymorphically pure or as substantially free of any other solid state (or polymorphic) forms. As used herein in this context, the expression "substantially free of any other forms" will be understood to mean that the solid state form of Rigosertib Sodium contains about 20% (w/w) or less, about 10% (w/w) or less, about 5% (w/w) or less, about 2% (w/w) or less, about 1% (w/w) or less, or about 0.5% (w/w) or less or about 0% of any other forms of the subject compound as measured, for example, by XRPD. Thus, solid state Forms A-E of Rigosertib Sodium described herein as substantially free of any other solid state forms would be understood to contain greater than about 80% (w/w), greater than about 90% (w/w), greater than about 95% (w/w), greater than about 98% (w/w), greater than about 99% (w/w), greater than about 99.5% (w/w), or about 100% of the subject crystalline polymorph of Rigosertib Sodium. In some embodiments of the disclosure, the described crystalline polymorph of Rigosertib Sodium may contain from about 0.5% to about 20% (w/w), from about 5% to about 20% (w/w), or from about 5% to about 10% (w/w) of one or more other solid state forms of Rigosertib Sodium.

As used herein, unless stated otherwise, reference to % values are to wt %. This is based on the assumption that the solvent % in the various forms is measured in wt %.

As used herein, and unless stated otherwise, the term "anhydrous" in relation to crystalline forms of Rigosertib Sodium, relates to a crystalline form of Rigosertib Sodium which does not include any crystalline water (or other solvents) in a defined, stoichiometric amount within the crystal. Moreover, an "anhydrous" form would not contain more than 1% (w/w) of either water or organic solvents as measured for example by TGA (Thermal Gravimetric Analysis) or by any other suitable technique.

The term "solvate," as used herein and unless indicated otherwise, refers to a crystal form that incorporates a solvent in the crystal structure. When the solvent is water, the solvate is often referred to as a "hydrate." The solvent in a solvate may be present in either a stoichiometric or in a non-stoichiometric amount. The term "solvate/hydrate", as used herein refers to a crystal form that incorporates a solvent and also water in the crystal structure, while both solvent and water may be present in either a stoichiometric or in a non-stoichiometric amount.

As used herein the term non-hygroscopic in relation to crystalline Rigosertib Sodium refers to less than 1.0% (w/w) absorption of water, by the crystalline Rigosertib Sodium as determined, for example, by TGA when exposed to 60% RH for 7 days at RT, or preferably 80% RH for 7 days at RT.

As used herein, and unless indicated otherwise, the term "wet crystalline form" refers to a polymorph that was not dried using any conventional techniques to remove residual solvent. Examples for such conventional techniques can be, but not limited to, evaporation, vacuum drying, oven drying, drying under nitrogen flow, etc.

As used herein, and unless indicated otherwise, the term "dry crystalline form" refers to a polymorph that was dried using any conventional techniques to remove residual solvent. Examples for such conventional techniques can be, but not limited to, evaporation, vacuum drying, oven drying, drying under nitrogen flow, etc.

As used herein, the term "isolated" in reference to a crystalline polymorph of Rigosertib Sodium of the present disclosure corresponds to a crystalline polymorph of Rigosertib Sodium that is physically separated from the reaction mixture in which it is formed.

As used herein, unless stated otherwise, the XRPD measurements are taken using copper Kα radiation wavelength 1.5418 Å. XRPD peaks reported herein are measured using CuK α radiation, λ=1.5418 Å, at a temperature of 25±3° C.

As used herein, unless stated otherwise, $^{13}$C solid state NMR was measured on 400 MHz at room temperature at a spin rate of 11 kHz.

A thing, e.g., a reaction mixture, may be characterized herein as being at, or allowed to come to "room temperature" or "ambient temperature", often abbreviated as "RT." This means that the temperature of the thing is close to, or the same as, that of the space, e.g., the room or fume hood, in which the thing is located. Typically, room temperature is from about 20° C. to about 30° C., or about 22° C. to about 27° C., or about 25° C.

The amount of solvent employed in a chemical process, e.g., a reaction or crystallization, may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding solvent X (1.5 v/v) to a 100 ml reaction mixture would indicate that 150 mL of solvent X was added.

A process or step may be referred to herein as being carried out "overnight." This refers to a time interval, e.g., for the process or step, that spans the time during the night, when that process or step may not be actively observed. This time interval is from about 8 to about 20 hours, or about 10-18 hours, in embodiments about 16 hours.

As used herein, the term "reduced pressure" refers to a pressure that is less than atmospheric pressure. For example, reduced pressure is about 10 mbar to about 50 mbar.

As used herein the term "substantially amorphous" of Rigosertib Sodium refers to a substantially amorphous form having an XRPD pattern possessing broad and undefined peaks as shown herein in FIG. 6.

The present disclosure includes a crystalline polymorph of Rigosertib Sodium, designated Form A. The crystalline Form A of Rigosertib Sodium may be characterized by data selected from one or more of the following: an X-ray powder diffraction pattern substantially as depicted in FIG. 1; an X-ray powder diffraction pattern having peaks at 13.4, 17.6, 18.4, 22.2 and 22.8 degrees 2-theta±0.2 degrees 2-theta; a solid state $^{13}$C NMR spectrum having peaks at 177.6, 159.3, 147.8, 138.1 and 108.6 ppm±0.2 ppm; a solid state $^{13}$C NMR spectrum having the following chemical shift absolute differences from a reference peak at 102.4 ppm±2 ppm of 75.2, 56.9, 45.4, 35.7 and 6.2 ppm±0.1 ppm; a solid state $^{13}$C NMR spectrum substantially as depicted in FIG. 7, 8 or 9, and/or combinations of these data.

Crystalline Form A of Rigosertib Sodium may be further characterized by an X-ray powder diffraction pattern having peaks at 13.4, 17.6, 18.4, 22.2 and 22.8 degrees 2-theta±0.2 degrees 2-theta, and also having any one, two, three, four or five additional peaks selected from 11.5, 25.5, 26.7, 28.4 and 29.5 degrees 2-theta±0.2 degrees 2-theta.

Crystalline Form A of Rigosertib Sodium may alternatively be characterized by an XRPD pattern having peaks at 11.5, 13.4, 17.6, 18.4, 22.2, 25.5, 22.8, 26.7, 28.4 and 29.5 degrees 2-theta±0.2 degrees 2-theta.

Crystalline Form A of Rigosertib Sodium may be characterized by each of the above characteristics alone/or by all possible combinations, e.g., an XRPD pattern having peaks at 13.4, 17.6, 18.4, 22.2 and 22.8 degrees 2-theta±0.2 degrees 2-theta; an XRPD pattern as depicted in FIG. 1, and combinations thereof. Crystalline Form A of Rigosertib Sodium may be in the form of a solvate, preferably wherein the solvate is selected from ethanolate, ipanolate or methyl acetate solvate. Optionally, Form A as defined by any combination of the above XRPD and/or solid state $^{13}$C NMR data, may be an ethanol solvate (e.g. a monoethanol solvate) or an ipanolate solvate (e.g. a hemi-ipanolate solvate). In certain embodiments, Form A as defined by any combination of the above XRPD and/or solid state $^{13}$C NMR data, may contain from about 6% to about 10% of ethanol or IPA by weight, preferably from about 7% to about 9%, and more preferably about 8% of ethanol or IPA by weight as determined for example by TGA or by any other suitable techniques.

The Form A as defined by any combination of the above XRPD and/or solid state $^{13}$C NMR data, in the form of an ethanolate (e.g. a monoethanol solvate) solvate or an ipanolate solvate (e.g. a hemi-ipanoate solvate) may additionally contain water in a stoichiometric or non-stoichiometric amount. In particular, the present disclosure encompasses Form A as defined by any combination of the above XRPD and/or solid state $^{13}$C NMR data, wherein the Form A is an ethanolate, ipanolate or methyl acetate solvate, wherein each may contain about 7-14% water. The present disclosure further encompasses form A as defined by any combination of the above XRPD and/or solid state $^{13}$C NMR data, optionally in the form of an ethanolate solvate (e.g. a monoethanol solvate), including about 6% to about 10% of ethanol (by weight), preferably from about 7% to about 9%, and more preferably about 8% of ethanol, and further comprising about 7 to about 14% (wt %) water. The present disclosure further encompasses Form A as defined by any combination of the above XRPD and/or solid state $^{13}$C NMR data, in the form of an ipanolate solvate (e.g. a hemi-ipanolate solvate), including about 6% to about 10% of isopropanol (by weight), preferably from about 7% to about 9%, and more preferably about 8% of isopropanol, and further including about 7 to about 14% (wt %) water. The present invention further encompasses the Form A as defined by any combination of the above XRPD and/or solid state $^{13}$C NMR data, in the form of a methylacetate solvate (e.g. a mono methylacetate solvate), including about 11% to about 15% of methyl acetate, preferably from about 12 to about 14%, more preferably about 13% methyl acetate, and further including about 7 to about 14% (wt %) water. In particular, the present disclosure encompasses Form A as defined by any combination of the above XRPD and/or solid state $^{13}$C NMR data, wherein the Form A is an ethanolate, ipanolate or methyl acetate solvate, wherein each may contain about 7 to about 14% water.

As described above, depending on which other solid state it is compared with, Form A of Rigosertib Sodium according to the present disclosure may have advantageous properties as described above. For example, Rigosertib Sodium Form A is stable and non-hygroscopic. For example, Form A according to any aspect or embodiment of the present disclosure as herein described, is substantially non-hygroscopic at e.g. up to about 80% relative humidity (for example for about 7 days at a temperature of 25° C.).

In another embodiment of the present disclosure, crystalline Form A of Rigosertib Sodium as described in any embodiment herein is polymorphically pure.

In an embodiment of the present disclosure, crystalline Form A of Rigosertib Sodium as described in any embodiment herein is isolated.

Rigosertib Sodium Form A may be prepared by a process including crystallization of Rigosertib Sodium in a mixture of ethanol or IPA in water, optionally isolating the Rigosertib Sodium Form A, and optionally drying.

The process preferably includes preparing a solution of Rigosertib Sodium in ethanol and water or IPA and water, heating the mixture, and optionally isolating Rigosertib Sodium Form A.

Preferably, the volume ratio of ethanol to water is about 25:1 to about 5:1, about 20:1 to about 10:1 and preferably about 19:1 or 9:1 (v/v).

Preferably, the volume ratio of IPA to water is about 20:1 to about 5:1, about 15:1 to about 6:1 and preferably about 9:1 (v/v).

Preferably, about 5 to about 12 vol, about 8 to about 11 vol, and particularly about 10 vol, of solution (mixture of ethanol or IPA in water) is used relative to Rigosertib Sodium.

The mixture of Rigosertib Sodium in ethanol and water is preferably heated to a temperature of about 60 to about 78° C., preferably about 70 to about 78° C., and more preferably about 75° C. Preferably, the heating is carried out over a period of about 30 to about 240 minutes, about 60 to about 200 minutes, about 100 to about 150 minutes, or about 120 minutes.

The mixture of Rigosertib Sodium in IPA and water is preferably heated to a temperature of about 60 to about 90° C., preferably about 70 to about 85° C. and more preferably about 80° C. Preferably, the heating is carried out over a period of about 30 to about 240 minutes, about 60 to about 200 minutes, about 100 to about 150 minutes or about 120 minutes.

The mixture may be optionally maintained at the elevated temperature for a period of: about 10 to about 120 minutes, about 10 to about 60 minutes, and particularly about 30 minutes, optionally with stirring.

The clear solution is preferably cooled prior to isolating the Rigosertib Sodium Form A. Preferably, the hot solution is cooled to a temperature of about 30 to about 0° C., in embodiments about 20 to about 0° C., in other embodiments to 10 to about 0° C., preferably to 5° C., optionally with stirring. Typically, the cooled mixture is a suspension. Preferably, the cooling is carried out over a period of about 30 to about 240 minutes, about 60 to about 200 minutes, about 100 to about 150 minutes, or about 120 minutes.

Prior to isolation of the Rigosertib Sodium Form A, the suspension is optionally maintained for an additional about 10 minutes to about 24 hours, preferably about 30 minutes to about 10 hours, preferably about 30 minutes to about 5 hours, more preferably about 1 hour, preferably wherein the temperature is maintained at 5° C. during this time period, optionally with stirring.

In embodiments, isolation of Rigosertib Sodium Form A may be done, for example, by filtering the resulting suspension and optionally drying. The drying may be carried out in air (e.g. by a stream of air or nitrogen during filtration), and may optionally further include drying at an elevated temperature and/or under reduced pressure. Drying is preferably done by nitrogen or air or under vacuum. Preferably, drying is performed at a temperature of about 40 to about 80° C., about 40 to about 60° C. or preferably about 50° C. When the drying is carried out under vacuum, preferably a reduced pressure of: about 1 to about 200 mbar, about 1 to about 100 mbar, about 1 to about 50 mbar, and particularly about 1 to about 20 mbar or, most particularly, about 10 mbar, is used.

The above processes for preparing Rigosertib Sodium Form A according to any embodiment may further include a step of combining the Rigosertib Sodium Form A with at least one pharmaceutically acceptable excipient to form a pharmaceutical composition or a pharmaceutical formulation.

The present disclosure further encompasses a crystalline polymorph of Rigosertib Sodium, designated Form B. The crystalline Form B of Rigosertib Sodium may be characterized by data selected from one or more of the following: an X-ray powder diffraction pattern substantially as depicted in FIG. 2; an X-ray powder diffraction pattern having peaks at 8.5, 18.8, 24.1, 29.4 and 31.7 degrees 2-theta±0.2 degrees 2-theta; and combinations of these data.

Crystalline Form B of Rigosertib Sodium may be further characterized by an X-ray powder diffraction pattern having peaks at 8.5, 18.8, 24.1, 29.4 and 31.7 degrees 2-theta±0.2 degrees 2-theta, and also having any one, two, three or four additional peaks selected from 17.5, 26.1, 26.7 and 35.0 degrees 2-theta±0.2 degrees 2-theta.

Crystalline Form B of Rigosertib Sodium may alternatively be characterized by an XRPD pattern having peaks at 8.5, 17.5, 18.8, 24.1, 26.1, 26.7, 29.4, 31.7 and 35.0 degrees 2-theta±0.2 degrees 2-theta.

Crystalline Form B of Rigosertib Sodium may be characterized by each of the above characteristics alone/or by all possible combinations, e.g., an XRPD pattern having peaks at 8.5, 18.8, 24.1, 29.4 and 31.7 degrees 2-theta±0.2 degrees 2-theta; an XRPD pattern as depicted in FIG. 2, and combinations thereof.

In another embodiment of the present disclosure, crystalline Form B of Rigosertib Sodium as described in any embodiment herein is polymorphically pure.

In an embodiment of the present disclosure, crystalline Form B of Rigosertib Sodium as described in any embodiment herein is isolated.

The present disclosure encompasses a crystalline polymorph of Rigosertib Sodium, designated Form C. The crystalline Form C of Rigosertib Sodium may be characterized by data selected from one or more of the following: an X-ray powder diffraction pattern substantially as depicted in FIG. 3; an X-ray powder diffraction pattern having peaks at 9.5, 11.9, 12.5, 16.4 and 21.2 degrees 2-theta±0.2 degrees 2-theta; and combinations of these data.

Crystalline Form C of Rigosertib Sodium may be further characterized by an X-ray powder diffraction pattern having peaks at 9.5, 11.9, 12.5, 16.4 and 21.2 degrees 2-theta±0.2 degrees 2-theta, and also having any one, two, three, four or five additional peaks selected from f 8.9, 13.3, 16.8, 17.5 and 24.6 degrees 2-theta±0.2 degrees 2-theta.

Crystalline Form C of Rigosertib Sodium may alternatively be characterized by an XRPD pattern having peaks at 8.9, 9.5, 11.9, 12.5, 13.3, 16.4, 16.8, 17.5, 21.2 and 24.6 degrees 2-theta±0.2 degrees 2-theta.

Crystalline Form C of Rigosertib Sodium may be characterized by each of the above characteristics alone/or by all possible combinations, e.g., an XRPD pattern having peaks at 9.5, 11.9, 12.5, 16.4 and 21.2 degrees 2-theta±0.2 degrees 2-theta; an XRPD pattern as depicted in FIG. 3, and combinations thereof.

In another embodiment of the present disclosure, crystalline Form C of Rigosertib Sodium as described in any embodiment herein is polymorphically pure.

In an embodiment of the present disclosure, crystalline Form C of Rigosertib Sodium as described in any embodiment herein is isolated.

The present disclosure encompasses a crystalline polymorph of Rigosertib Sodium, designated Form D. The crystalline Form D of Rigosertib Sodium may be characterized by data selected from one or more of the following: an X-ray powder diffraction pattern substantially as depicted in FIG. 4; an X-ray powder diffraction pattern having peaks at 10.3, 11.7, 13.9, 20.7 and 21.8 degrees 2-theta±0.2 degrees 2-theta; and combinations of these data.

Crystalline Form D of Rigosertib Sodium may be further characterized by an X-ray powder diffraction pattern having peaks at 10.3, 11.7, 13.9, 20.7 and 21.8 degrees 2-theta±0.2 degrees 2-theta, and also having any one, two, three, four or five additional peaks selected from 14.6, 17.8, 19.5 and 23.1 degrees 2-theta±0.2 degrees 2-theta.

Crystalline Form D of Rigosertib Sodium may alternatively be characterized by an XRPD pattern having peaks at 10.3, 11.7, 13.9, 14.6, 17.8, 19.5, 20.7, 21.8 and 23.1 degrees 2-theta±0.2 degrees 2-theta.

Crystalline Form D of Rigosertib Sodium may be characterized by each of the above characteristics alone/or by all possible combinations, e.g., an XRPD pattern having peaks at 10.3, 11.7, 13.9, 20.7 and 21.8 degrees 2-theta±0.2 degrees 2-theta; an XRPD pattern as depicted in FIG. 4, and combinations thereof.

In another embodiment of the present disclosure, crystalline Form D of Rigosertib Sodium as described in any embodiment herein is polymorphically pure.

In an embodiment of the present disclosure, crystalline Form D of Rigosertib Sodium as described in any embodiment herein is isolated.

The present disclosure encompasses a crystalline polymorph of Rigosertib Sodium, designated Form E. The crystalline Form E of Rigosertib Sodium may be characterized by data selected from one or more of the following: an X-ray powder diffraction pattern substantially as depicted in FIG. 5; an X-ray powder diffraction pattern having peaks at 10.8, 11.9, 14.3, 18.7 and 19.3 degrees 2-theta±0.2 degrees 2-theta; a solid state $^{13}$C NMR spectrum having peaks at 175.0, 146.9, 145.4, 121.6 and 102.8 ppm±0.2 ppm; a solid state $^{13}$C NMR spectrum having the following chemical shift absolute differences from a reference peak at 101.5 ppm±2 ppm of 73.5, 45.4, 43.9, 20.1 and 1.3 ppm±0.1 ppm; a solid state $^{13}$C NMR spectrum substantially as depicted in FIG. 10, 11 or 12, and/or combinations of these data.

Crystalline Form E of Rigosertib Sodium may be further characterized by an X-ray powder diffraction pattern having peaks at 10.8, 11.9, 14.3, 18.7 and 19.3 degrees 2-theta±0.2 degrees 2-theta, and also having any one, two, three, four or five additional peaks selected from 4.0, 12.3, 12.8, 21.4 and 22.7 degrees 2-theta±0.2 degrees 2-theta.

Crystalline Form E of Rigosertib Sodium may alternatively be characterized by an XRPD pattern having peaks at 4.0, 10.8, 11.9, 12.3, 12.8, 14.3, 18.7, 19.3, 21.4 and 22.7 degrees 2-theta±0.2 degrees 2-theta.

Crystalline Form E of Rigosertib Sodium may be characterized by each of the above characteristics alone/or by all possible combinations, e.g., an XRPD pattern having peaks at 10.8, 11.9, 14.3, 18.7 and 19.3 degrees 2-theta±0.2 degrees 2-theta; an XRPD pattern as depicted in FIG. 5; and combinations thereof.

Crystalline Form E of Rigosertib Sodium may be characterized as solvate form, while the solvate can be selected from ethanolate or methanolate. In certain embodiments, Form E may contain from about 7% to about 10% of ethanol by weight, preferably from about 7% to about 9%, and more preferably about 7.8% of ethanol by weight as determined for example by TGA or by any other suitable techniques. The present disclosure further encompasses form E as defined by any combination of the above XRPD and/or solid state $^{13}$C NMR data, optionally in the form an ethanol solvate (e.g. a monoethanol solvate). The present disclosure further encompasses form E as defined by any combination of the above XRPD and/or solid state $^{13}$C NMR data, optionally in the form an ethanol solvate (e.g. a monoethanol solvate), optionally including from about 7% to about 10% of ethanol by weight, preferably from about 7% to about 9%, and more preferably about 7.8% of ethanol by weight as determined, for example, by TGA or by any other suitable techniques. In certain embodiments, Form E may contain from about 6% to about 10% of methanol by weight, preferably from about 7% to about 8%, and more preferably about 7.7% of methanol by weight as determined, for example, by TGA or by any other suitable techniques. The present disclosure further encompasses form E as defined by any combination of the above XRPD and/or solid state $^{13}$C NMR data, optionally in the form a methanol solvate (e.g. a hemi-methanol solvate). The present disclosure further encompasses form E as defined by any combination of the above XRPD and/or solid state $^{13}$C NMR data, optionally in the form of a methanol solvate (e.g. a hemi-methanol solvate), optionally including from about 6% to about 10% of methanol by weight, preferably from about 7% to about 8%, and more preferably about 7.7% of methanol by weight as determined, for example, by TGA or by any other suitable techniques.

In another embodiment of the present disclosure, crystalline Form E of Rigosertib Sodium as described in any embodiment herein is polymorphically pure.

In an embodiment of the present disclosure, crystalline Form E of Rigosertib Sodium as described in any embodiment herein is isolated.

As described above, depending on which other solid state it is compared with, Form E of Rigosertib Sodium according to the present disclosure may have advantageous properties as described above. For example, Rigosertib Sodium Form E is stable for at least 4M at RT.

The above Rigosertib Sodium Form E can be prepared by a process including exposure of Rigosertib Sodium in aqueous solution to ethanol or methanol vapors.

Preferably, about 2 to about 20 vol, about 3 to about 10 vol, about 3 to about 5 vol, and preferably about 4 vol of water is used to dissolve Rigosertib Sodium.

Preferably, the aqueous solution is kept under ethanol or methanol vapors at temperature of about 2 to about 10° C., about 2 to 6° C., preferably about 4° C., for about 1 to about 10 days, about 2 to about 8 days, and particularly about 4 days.

In preferred embodiments, isolation of Rigosertib Sodium may be done, for example, by filtering the resulting suspension and optionally drying. Drying is preferably done by nitrogen or air or under vacuum. Preferably, drying is performed at a temperature of about 10 to about 30° C., about 15 to about 25° C., or preferably about 20° C. When the drying is carried out under vacuum, preferably a reduced pressure of: about 1 to about 200 mbar, about 1 to about 100 mbar, about 1 to about 50 mbar, and particularly about 1 to about 20 mbar or most particularly, about 10 mbar, is used.

The above processes for preparing Rigosertib Sodium Form E according to any embodiment may further include a step of combining the Rigosertib Sodium Form E with at least one pharmaceutically acceptable excipient to form a pharmaceutical composition or a pharmaceutical formulation.

The present disclosure also relates to the uses of any one or a combination of the crystalline polymorphs of Rigosertib Sodium of the present disclosure, for preparing other crystalline polymorphs or other solid state forms of Rigosertib. For instance, substantially amorphous Rigosertib Sodium can be used for the preparation of Rigosertib Sodium Forms B, C and D.

The present disclosure also relates to any one or a combination of the above described crystalline polymorphs of Rigosertib Sodium of the present disclosure, for use in the preparation of other crystalline polymorphs or other solid state forms of Rigosertib Sodium.

In another aspect, the present disclosure encompasses any one or combination of the above described crystalline polymorphs of Rigosertib Sodium for use in the preparation of pharmaceutical compositions and/or formulations for use in medicine, in embodiments for the treatment of Chronic myelomonocytic leukemia and Myelodysplastic syndromes.

In another embodiment, the present disclosure also encompasses the uses of any one or combination of the above described crystalline polymorphs of Rigosertib Sodium for the preparation of pharmaceutical compositions and/or formulations for use in medicine, in embodiments for the treatment of Chronic myelomonocytic leukemia and Myelodysplastic syndromes.

The present disclosure includes processes for preparing the above mentioned pharmaceutical compositions. The processes encompass combining any one of the above crystalline polymorphs of Rigosertib Sodium and/or combinations thereof of the present disclosure with at least one pharmaceutically acceptable excipient.

Pharmaceutical formulations of the present invention contain any one or a combination of the crystalline polymorphs of Rigosertib Sodium including crystalline Rigosertib Sodium Forms A-E. In addition to the active ingredient, the pharmaceutical formulations of the present disclosure can contain one or more excipients. Excipients are added to the formulation for a variety of purposes.

Diluents increase the bulk of a solid pharmaceutical composition, and can make a pharmaceutical dosage form containing the composition easier for the patient and caregiver to handle. Diluents for solid compositions include, for example, microcrystalline cellulose (e.g., Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., Eudragit®), potassium chloride, powdered cellulose, sodium chloride, sorbitol, and talc.

Solid pharmaceutical compositions that are compacted into a dosage form, such as a tablet, can include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate, and starch.

The dissolution rate of a compacted solid pharmaceutical composition in the patient's stomach can be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®), and starch.

Glidants can be added to improve the flowability of a non-compacted solid composition and to improve the accuracy of dosing. Excipients that can function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that can be included in the composition of the present invention include maltol, vanillin, ethyl vanillin, menthol, citric acid, fumaric acid, ethyl maltol, and tartaric acid.

Solid and liquid compositions can also be dyed using any pharmaceutically acceptable colorant to improve their appearance and/or facilitate patient identification of the product and unit dosage level.

In liquid pharmaceutical compositions of the present invention, Rigosertib Sodium and any other solid excipients are dissolved or suspended in a liquid carrier such as water, vegetable oil, alcohol, polyethylene glycol, propylene glycol, or glycerin.

Liquid pharmaceutical compositions can contain emulsifying agents to disperse uniformly throughout the composition an active ingredient or other excipient that is not soluble in the liquid carrier. Emulsifying agents that can be useful in liquid compositions of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions of the present invention can also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, and xanthan gum.

Sweetening agents such as sorbitol, saccharin, sodium saccharin, sucrose, aspartame, fructose, mannitol, and invert sugar can be added to improve the taste.

Preservatives and chelating agents such as alcohol, sodium benzoate, butylated hydroxyl toluene, butylated hydroxyanisole, and ethylenediamine tetraacetic acid can be added at levels safe for ingestion to improve storage stability.

According to the present disclosure, a liquid composition can also contain a buffer such as gluconic acid, lactic acid, citric acid, or acetic acid, sodium gluconate, sodium lactate, sodium citrate, or sodium acetate. Selection of excipients and the amounts used can be readily determined by the formulation scientist based upon experience and consideration of standard procedures and reference works in the field.

The solid compositions of the present disclosure include powders, granulates, aggregates, and compacted compositions. The dosages include dosages suitable for oral, buccal, rectal, parenteral (including subcutaneous, intramuscular, and intravenous), inhalant, and ophthalmic administration. Although the most suitable administration in any given case will depend on the nature and severity of the condition being treated in embodiments, the route of administration is oral. The dosages can be conveniently presented in unit dosage form and prepared by any of the methods well-known in the pharmaceutical arts.

Dosage forms include solid dosage forms like tablets, powders, capsules, suppositories, sachets, troches, and lozenges, as well as liquid syrups, suspensions, and elixirs.

The dosage form of the present disclosure can be a capsule containing the composition, in embodiments a powdered or granulated solid composition of the invention, within either a hard or soft shell. The shell can be made from gelatin and optionally contain a plasticizer such as glycerin and sorbitol, and an opacifying agent or colorant.

The active ingredient and excipients can be formulated into compositions and dosage forms according to methods known in the art.

A composition for tableting or capsule filling can be prepared by wet granulation. In wet granulation, some or all of the active ingredients and excipients in powder form are blended and then further mixed in the presence of a liquid, typically water, which causes the powders to clump into granules. The granulate is screened and/or milled, dried, and then screened and/or milled to the desired particle size. The granulate can then be tableted, or other excipients can be added prior to tableting, such as a glidant and/or a lubricant.

A tableting composition can be prepared conventionally by dry blending. For example, the blended composition of the actives and excipients can be compacted into a slug or a sheet and then comminuted into compacted granules. The compacted granules can subsequently be compressed into a tablet.

As an alternative to dry granulation, a blended composition can be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate, and colloidal silica. The proper use of these and other excipients in direct compression tableting is known to those in the art with experience and skill in particular formulation challenges of direct compression tableting.

A capsule filling of the present invention can include any of the aforementioned blends and granulates that were described with reference to tableting, but they are not subjected to a final tableting step.

A pharmaceutical formulation of Rigosertib Sodium can be administered. Rigosertib Sodium can be formulated for administration to a mammal, such as a human, by injection. Rigosertib Sodium can be formulated, for example, as a viscous liquid solution or suspension, in embodiments a clear solution, for injection. The formulation can contain one or more solvents. A suitable solvent can be selected by considering the solvent's physical and chemical stability at various pH levels, viscosity (which would allow for syringeability), fluidity, boiling point, miscibility, and purity. Suitable solvents include alcohol USP, benzyl alcohol NF, benzyl benzoate USP, and Castor oil USP. Additional substances can be added to the formulation such as buffers, solubilizers, and antioxidants, among others. Ansel et al., Pharmaceutical Dosage Forms and Drug Delivery Systems, 7th ed.

The crystalline polymorphs of Rigosertib Sodium and the pharmaceutical compositions of Rigosertib Sodium of the present disclosure can be used as medicaments, particularly in the treatment of Chronic myelomonocytic leukemia and Myelodysplastic syndromes.

In another embodiment, Rigosertib Forms A-E and the pharmaceutical compositions of Rigosertib Forms A-E can be used as medicaments, particularly in the treatment of Chronic myelomonocytic leukemia and Myelodysplastic syndromes.

The present disclosure also provides methods of treating Chronic myelomonocytic leukemia and Myelodysplastic syndromes by administering a therapeutically effective amount of crystalline polymorphs of Rigosertib Sodium of the present disclosure, or at least one of the above pharmaceutical compositions, to a subject in need of the treatment.

Having thus described the disclosure with reference to particular embodiments and illustrative examples, those in the art can appreciate modifications to the disclosure as described and illustrated that do not depart from the spirit and scope of the disclosure as disclosed in the specification. The Examples are set forth to aid in understanding the disclosure but are not intended to, and should not be construed to limit its scope in any way.

Analytical Methods

Powder X-Ray Diffraction (XRD) Method

Powder X-ray Diffraction was performed on an X-Ray powder diffractometer PanAlytical X'pert Pro; CuKα radiation (λ=1.54187 Å); X'Celerator detector with active length 2.122 degrees 2-theta; laboratory temperature 25±3° C.; zero background sample holders. Prior to analysis, the samples were gently ground using a mortar and pestle to obtain a fine powder. The ground sample was adjusted into a cavity of the sample holder and the surface of the sample was smoothed using a cover glass.

Measurement Parameters:

| Scan range | 3-40 degrees 2-theta |
|---|---|
| Scan mode | continuous |
| Step size | 0.0167 degrees |
| Step size | 42 s |
| Sample spin | 60 rpm |
| Sample holder | zero background silicon plate |

$^{13}$C Solid State NMR Method:

$^{13}$C CP/MAS NMR spectra were measured at 125 MHz using Bruker Avance III 500 WB/US NMR spectrometer (Karlsruhe, Germany, 2003) at magic angle spinning (MAS) frequency $\omega_r/2\pi$=11 kHz. In all cases finely powdered samples were placed into 4-mm ZrO$_2$ rotors and the standard "cpmas" pulse program was used. During acquisition of the data the high-power dipolar decoupling "TPPM" (two-pulse phase-modulated) was applied. The flip-pulse length was 4.8 μs. Applied nutation frequency of B$_1$($^1$H) field was $\omega_1/2\pi$=89.3 kHz. Nutation frequency of B$_1$($^{13}$C) and B$_1$($^1$H) fields during cross-polarization was $\omega_1/2\pi$=62.5 kHz. The number of scans was 2048. Taking into account frictional heating of the samples during fast rotation all NMR experiments were performed at 293 K (precise temperature calibration was performed).

The NMR spectrometer was completely calibrated and all experimental parameters were carefully optimized prior the investigation of samples. Magic angle was set using KBr during standard optimization procedure and homogeneity of magnetic field was optimized using adamantane sample (resulting line-width at half-height $\Delta v_{1/2}$ was less than 3.5 Hz at 250 ms of acquisition time).

EXAMPLES

Substantially amorphous Rigosertib Sodium was used as the starting material in Examples 4-6. Substantially amorphous Rigosertib Sodium may be prepared by the procedure disclosed in U.S. Pat. No. 8,476,320. Rigosertib may be prepared by the procedure disclosed in U.S. Pat. No. 7,598,232.

Example 1. Preparation of Rigosertib Sodium Form A

Rigosertib Sodium (100 mg) was suspended into a mixture of ethanol (0.95 ml) and water (0.05 ml). The suspension was heated up to Tj (=Temperature of Jacket) 75° C. for 120 minutes, the suspension was dissolved at about 66° C., the solution was then cooled from 75° C. to 5° C. over 2 hours (crystal is out at about 60° C.) followed by keeping the suspension at 5° C. with stirring for 60 minutes. The suspension was filtered and the sample was kept for about 20 minutes on the filter for drying, followed by additional drying for 5 hours at 50° C. under stream of nitrogen. The sample was analyzed by XRD, as shown by FIG. 1, and confirmed Rigosertib Sodium Form A content.

Example 2. Preparation of Rigosertib Sodium Form A

Rigosertib Sodium (100 mg) was suspended into a mixture of ethanol (0.90 ml) and water (0.1 ml), the suspension was heated up to Tj (=Temperature of Jacket) 75° C. during 120 minutes, the suspension was dissolved at about 33° C., the solution was then cooled from 75° C. to 5° C. over 2 hours (crystal is out at about 21° C.) and the obtained suspension was kept at 5° C. with stirring for 60 minutes. The suspension was filtered and the sample was kept for about 20 minutes on the filter for drying, followed by additional drying for 5 hours at 50° C. under stream of nitrogen. XRD measurement confirmed Rigosertib Sodium Form A content.

Example 3. Preparation of Rigosertib Sodium Form A

Rigosertib Sodium (100 mg) was suspended into a mixture of isopropyl alcohol (0.90 ml) and water (1.0 ml). The suspension was heated up to Tj 80° C. during 120 minutes and the suspension was dissolved at about 70° C. The solution was kept at this temperature for about 30 minutes before cooling, and then temperature was reduced from 80° C. to 5° C. over 2 hours and further stirring the suspension at 5° C. for 60 minutes. Sample was filtered and the sample was kept for about 20 minutes on the filter for drying.

Example 4. Preparation of Rigosertib Sodium Form B

Rigosertib Sodium (80 mg, substantially amorphous) was suspended in cyclopentanone (1 ml). The suspension was heated up to Tj 129° C. during 2 hours and kept further at about 129° C. for 30 minutes with stirring. Afterwards, the suspension was cooled down to Tj 0° C. and was kept at this temperature for additional 60 min with stirring. Sample was filtered and kept on the filter glass for 20 minutes for drying. The analyzed sample confirms Form B content, as described in FIG. 2.

Example 5. Preparation of Rigosertib Sodium Form C

Rigosertib Sodium (about 30 mg, substantially amorphous) was put on aluminum pan and placed into a DVS instrument (Dynamic Vapor Sorption). The following conditions were used for this experiment in the DVS: the relative humidity was increased from 0% RH to 90% RH and then decreased back to 0% RH at 25° C. The used step size was 10% RH and condition for the next step: dm/dt 0.002. Afterwards, the sample was removed from aluminum pan, placed on XRPD sample holder and analyzed by XRD, confirming Form C content, as shown in FIG. 3.

Example 6. Preparation of Rigosertib Sodium Form D

Rigosertib Sodium (100 mg, substantially amorphous) was exposed to 100% RH for 5 days at RT. XRD measurement, shown in FIG. 4, confirmed Form D content.

Example 7. Preparation of Rigosertib Sodium Form E

Rigosertib Sodium (100 mg) was dissolved in a vial with water (400 ml). This vial (kept open) was placed into another bigger bottle containing ethanol inside. The bottle with the open vial inside, was kept closed for 5 days at 4° C. in order to produce ethanol vapor environment in the sample vial. Keeping the vial sample under ethanol allowed the vapors to slowly diffuse into the sample and form white crystals of Rigosertib Sodium. Crystals were recovered by filtration and dried by a stream of nitrogen at 20° C. XRD diffractogram described in FIG. 5 confirmed Form E content.

The above procedure can be used also by placing the vial with Rigosertib solution in water into another bigger bottle containing methanol inside, instead of ethanol and using the same procedure described above.

Example 8. Preparation of Rigosertib Sodium Form A

Rigosertib Sodium (50 mg) was fully dissolved in a mixture of methanol/water (4:1 v/v, 400 µl) at 20° C. The vial containing clear solution was transferred to the bath of Huber thermostat set at −20° C. After the cooling, methyl acetate was added drop by drop with stirring. After a volume 3 ml was added, the solution became turbid. Then the mixture methanol/water (4:1 v/v, 200 µl) and methyl acetate (4 ml) was added and solution was maintained at −20° C. one hour. After that the vial was removed from the bath and allowed to stand at 20° C. Needle Form A crystals were formed on the vial walls within three days.

Example 9. Preparation of Rigosertib Sodium Form E

Rigoserib sodium (50 mg) was dissolved in a mixture of methanol/water (4:1 v/v, 400 ul) and cooled to −20° C. Ethyl formate (4 ml) was added with stirring at −20° C. and the solution was maintained at −20° C. for additional 30 minutes. Then the solution was allowed to warm spontaneously to 20° C. and crystallized overnight. Crystals formed were recovered by filtration and dried on air. XRPD measurement confirmed Form E.

Example 10. Preparation of Rigosertib Sodium Form E

Rigosertib Sodium (0.1 grams) was dissolved in a vial with water (0.4 ml). This vial (kept open) was placed into another bigger bottle containing ethanol inside. The bottle with the open vial inside, was kept closed for 5 days at 4° C. in order to produce ethanol vapor environment in the sample vial. White crystals of Rigosertib Sodium were formed and recovered by filtration. The product was dried by a stream of nitrogen at 20° C. XRPD diffractogram confirmed Form E content. This procedure can be carried out using methanol instead of ethanol.

The invention claimed is:
1. A crystalline Form E of Rigosertib Sodium, characterized by data selected from one or more of the following:
   a) an XRPD pattern having peaks at 10.8, 11.9, 14.3, 18.7 and 19.3 degrees 2-theta±0.2 degrees 2-theta;
   b) an XRPD pattern as depicted in FIG. 5;
   c) a solid state ¹³C NMR spectrum having peaks at 175.0, 146.9, 145.4, 121.6 and 102.8 ppm=0.2 ppm;
   d) a solid state ¹³C NMR spectrum having the following chemical shift absolute differences from a reference peak at 101.5 ppm±2 ppm of 73.5, 45.4, 43.9, 20.1 and 1.3 ppm±0.1 ppm;
   e) a solid state ¹³C NMR spectrum as depicted in FIG. 10, 11, or 12; and
   f) a combination of any one or more of (a), (b), (c), (d) and (e).

2. The crystalline Form E of Rigosertib Sodium according to claim 1, characterized by data selected from one or more of the following: an XRPD pattern having peaks at 10.8, 11.9, 14.3, 18.7 and 19.3 degrees 2-theta±0.2 degrees 2-theta; and also having one, two, three, four or five additional peaks selected from the group consisting of 4.0, 12.3, 12.8, 21.4 and 22.7 degrees 2-theta±0.2 degrees 2-theta.

3. The crystalline Form E according to claim 1, which is selected from an ethanol solvate or a methanol solvate.

4. The crystalline Form E according to claim 1, wherein the crystalline form E contains 20% (w/w) or less of any other solid state forms of Rigosertib Sodium.

5. A pharmaceutical composition comprising the crystalline Form E according to claim 1.

6. A pharmaceutical formulation comprising the crystalline Form E according to claim 1 and at least one pharmaceutically acceptable excipient.

7. A process for preparing a pharmaceutical formulation comprising combining the crystalline Form E according to claim 1 with at least one pharmaceutically acceptable excipient.

8. A medicament comprising the crystalline Form E according to claim 1.

9. A method of treating Chronic myelomonocytic leukemia or Myelodysplastic syndromes, comprising administering a therapeutically effective amount of a crystalline Form E according to claim 1 to a subject suffering or otherwise in need of the treatment.

10. A process for preparing Rigosertib Sodium Form E according to claim 1, comprising exposing an aqueous solution of Rigosertib Sodium to ethanol or methanol vapors.

11. A process according to claim 10, wherein about 2 to about 20 vol of water is used to prepare Rigosertib Sodium solution.

12. A process according to claim 10, wherein the solution is maintained in ethanol or methanol vapors at a temperature of about 2 to about 10° C., for about 1 to about 10 days.

13. A process according to claim 10, wherein the Rigosertib Sodium Form E is isolated, and optionally washed, and optionally dried.

14. A process according to claim 13, wherein the Rigosertib Sodium Form E is dried under a stream of inert gas, at a temperature of about 10 to about 30° C.

15. A process according to claim 10, further comprising combining the Rigosertib Sodium Form E with at least one pharmaceutically acceptable excipient to form a pharmaceutical composition or a pharmaceutical formulation.

* * * * *